United States Patent [19]

Wang et al.

[11] Patent Number: 4,585,862
[45] Date of Patent: Apr. 29, 1986

[54] FLUORESCENCE POLARIZATION IMMUNOASSAY

[75] Inventors: Chao-Huei J. Wang, Gurnee; Stephen D. Stroupe, Libertyville; Michael E. Jolley, Round Lake, all of Ill.

[73] Assignee: Abbott Laboratories, Chicago, Ill.

[21] Appl. No.: 577,946

[22] Filed: Feb. 8, 1984

Related U.S. Application Data

[63] Continuation of Ser. No. 329,975, Dec. 11, 1981, abandoned.

[51] Int. Cl.$^4$ ............................................. G01N 33/52
[52] U.S. Cl. .................................... 544/319; 549/223; 549/225
[58] Field of Search .................. 549/223, 225; 544/319

[56] References Cited

U.S. PATENT DOCUMENTS 4,476,229  10/1984  Fino et al. ........................... 549/223

FOREIGN PATENT DOCUMENTS 56-121039  9/1981  Japan .

Primary Examiner—Maurice J. Welsh
Assistant Examiner—M. L. Moore
Attorney, Agent, or Firm—Margaret M. O'Brien; James L. Wilcox

[57] ABSTRACT

This disclosure relates to a method and reagents for determining ligands in biological fluids such as serum, plasma, spinal fluid, amnionic fluid and urine. In particular, this disclosure relates to a fluorescence polarization immunoassay procedure and to a novel class of tracer compounds employed as reagents in such procedures. The procedure disclosed combines the specificity of an immunoassay with the speed and convenience of fluorescence polarization techniques to provide a means for determining the amount of the specific ligand present in a sample.

56 Claims, No Drawings

FLUORESCENCE POLARIZATION IMMUNOASSAY

This is a continuation of application Ser. No. 329,975 filed Dec. 11, 1981 now abandoned.

BACKGROUND OF THE INVENTION

The present invention relates to a method and reagents for determining ligands in biological fluids such as serum, plasma, spinal fluid, amnionic fluid and urine. In particular, the present invention relates to a fluorescence polarization immunoassay procedure and to tracers employed as reagents in such procedures. The fluorescence polarization immunoassay procedure of the present invention combines the specificity of an immunoassay with the speed and convenience of fluorescence polarization techniques to provide a means for determining the amount of a specific ligand present in a sample.

Competitive binding immunoassays for measuring ligands are based on the competition between a ligand in a test sample and a labeled reagent, referred to as a tracer, for a limited number of receptor binding sites on antibodies specific to the ligand and tracer. The concentration of ligand in the sample determines the amount of tracer that will specifically bind to an antibody. The amount of tracer-antibody conjugate produced may be quantitively measured and is inversely proportional to the quantity of ligand in the test sample.

In general, fluorescence polarization techniques are based on the principle that a fluorescent label compound when excited by linearly polarized light will emit fluorescence having a degree of polarization inversely related to its rate of rotation. Therefore, when a molecule such as a tracer-antibody conjugate having a fluorescent label is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescence polarization provides a quantitive means for measuring the amount of tracer-antibody conjugate produced in a competitive binding immunoassay.

SUMMARY OF THE INVENTION

The present invention encompasses a method for determining ligands in a sample comprising intermixing with said sample a biologically acceptable salt of a tracer of the formula:

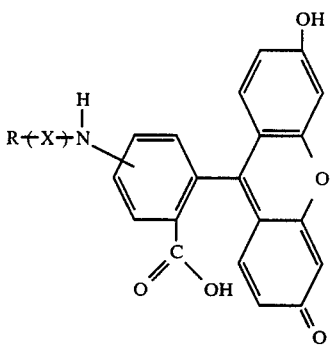

wherein X is a group selected from the class consisting of an oxalyl group of the formula:

a sulfonyl group of the formula:

and a carboamidosulfonyl group of the formula:

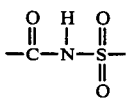

and
R is a ligand-analog wherein said ligand-analog has at least one common epitope with said ligand so as to be specifically reconizable by a common antibody; and an antibody capable of specifically recognizing said ligand and said tracer; and then determining the amount of tracer-antibody conjugate by fluorescence polarization techniques as a measure of the concentration of said ligand in the sample.

The invention further relates to a novel class of tracers of formula (I) and biologically acceptable salts thereof, which are useful as reagents in the above-described method. The methods and tracers of the present invention are particularly useful in quantitatively monitoring therapeutic drug concentrations in serum and plasma.

DETAILED DESCRIPTION OF THE INVENTION

The term "ligand" as used herein refers to a molecule in particular a low molecular weight hapten, to which a receptor, normally an antibody, can be obtained or formed. Haptens are protein-free bodies, generally of low molecular weight that do not induce antibody formation when injected into an animal, but are reactive to antibodies. Antibodies to hapten are generally raised by first conjugating the haptens to a protein and injecting the conjugate product into an animal. The resulting antibodies are isolated by conventional antibody isolation techniques.

The ligands determinable by the method of the present invention vary over a wide molecular weight range.

Although high molecular weight ligands may be determined, for best results, it is generally preferable to employ the methods of the present invention to determine ligands of low molecular weight, generally in a range of 50 to 4000. It is more preferred to determine ligands having a molecular weight in a range of 100 to 2000.

The novel tracer of the present invention includes compounds of formula (I) wherein the ligand-analog represented by R include radicals having a molecular weight within a range of 50 to 4000. The preferred novel tracers include compounds of formula (I) wherein the ligand-analogs represented by R include radicals having a molecular weight within a range of 100 to 2000.

Representative of ligands determinable by the methods of the present invention include steroids such as esterone, estradiol, cortisol, testosterone, progesterone, chenodeoxycholic acid, digoxin, cholic acid, digitoxin, deoxycholic acid, lithocholic acids and the ester and amide derivatives thereof; vitamins such as B-12, folic acid; thyroxine, triiodothyronine, histamine, serotonin, prostaglandins such as PGE, PGF, PGA; antiasthamatic drugs such as theophylline; antineoplastic drugs such as doxorubicin and methotrexate; antiarrhythmic drugs such as disopyramide, lidocaine, procainamide, propranolol, quinidine, N-acetylprocainamide; anticonvulsant drugs such as phenobarbital, phenytoin, primidone, valproic acid, carbamazepine and ethosuximide; antibiotics such as penicillins, cephalosporins, erythromycin, vancomycin, gentamicin, amikacin, chloramphenicol, streptomycin and tobramycin; antiarthritic drugs such as salicylate; antidepressant drugs including tricyclics such as nortriptyline, amitriptyline, imipramine and desipramine; and the like as well as the metabolites thereof. In addition, drugs of abuse such as morphine, heroin, hydromophone, oxymorphone, metapon, codeine, hydrocodone, dihydrocodiene, dihydrohydroxy codeinone, pholcodine, dextromethorphan, phenazocine and deonin and their metabolites may be determined in accordance with the methods of the present invention.

The tracers of the present invention generally exist in an equilibrium between their acid and ionized states, and in the ionized state are effective in the method of the present invention. Therefore, the present invention comprises the tracers in either the acid or ionized state and for convenience, the tracers of the present invention are structurally represented herein in their acid form. When the tracers of the present invention are present in their ionized state, the tracers exist in the form of biologically acceptable salts. As used herein, the term "biologically acceptable salts" refers to salts such as sodium, potassium, ammonium and the like which will enable the tracers of the present invention to exist in their ionized state when employed in the method of the present invention. Generally, the tracers of the present invention exist in solution as salts, the specific salt results from the buffer employed, i.e., in the presence of a sodium phosphate buffer, the tracers of the present invention will generally exist in their ionized state as a sodium salt.

The term "ligand-analog" as used herein refers to a mono- or polyvalent radical a substantial proportion of which has the same spatial and polar organization as the ligand to define one or more determinant or epitopic sites capable of competing with the ligand for the binding sites of a receptor. A characteristic of such ligand-analog is that it possesses sufficient structural similarity to the ligand of interest so as to be recognized by the antibody for the ligand. For the most part, the ligand analog will have the same or substantially the same structure and charge distribution (spatial and polar organization) as the ligand of interest for a significant portion of the molecular surface. Since frequently, the linking site for a hapten will be the same in preparing the antigen for production of antibodies as used for linking to the ligand, the same portion of the ligand analog which provides the template for the antibody will be exposed by the ligand analog in the tracer.

When X is a sulfonyl group,

the class of ligand-analogs represented by R are derived from the corresponding ligand by removal of an aromatic hydrogen, that is a hydrogen bonded to an aromatic carbon, preferably a phenyl carbon, or by the formation of a phenyl or substituted phenyl derivative of the ligand. In addition, a ligand may be structurally modified by the addition or election of one or more functional groups to form a ligand-analog while retaining the necessary epitope sites for binding to an antibody. However, it is preferred that such modified ligand-analogs be bonded to the sulfonylaminofluorescence moiety through an aromatic carbon.

When X is an oxalyl group,

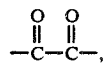

the class of ligand analogs represented by R are derived from the corresponding ligand by removal of a hydrogen atom bond to a reactive amine, i.e., a hydrogen atom bonded to a primary or secondary amine or by the formation of an amino derivative of the ligand wherein an imino group

replaces one or more atoms originally present in the ligand, at the site of binding to an oxalylaminofluorescein moiety. Illustrative of ligands which upon the removal of a hydrogen bond to a reactive amine from a ligand-analog represented by R include, for example, procainamide, thyroxine, quinidine and the aminoglycoside antibiotics. Illustrative of ligands whose amino derivatives are useful as ligand-analogs include theophylline, valproic acid, phenobarbital, phenytoin, primidone, disopyramide, digoxin, chloramphenicol, salicylate, acetaminophen, carbamazepine, desipramine and nortriptyline. In addition, a ligand may be structurally modified by the addition or deletion of one or more functional groups to form a ligand-analog, while retaining the necessary epitope sites for binding to an antibody. However, it is preferred that such modified ligand-analogs be bonded to the oxalylaminofluorescein moiety through an imino group.

When X is a carboamidosulfonylamino

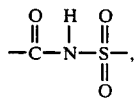

the class of ligand analogs represented by R are derived from the corresponding ligand by removal of a reactive hydrogen atom, i.e., a hydrogen atom bonded to a hydroxy oxygen or a reactive amine (primary or secondary) or by the formation of an amino derivative of the ligand wherein an limino group

replaces one or more atoms originally present in the ligand, at the site of binding to a carboamidosulfonyl-aminofluorescein moiety. Illustrative of ligands which upon the removal of a reactive hydrogen may form a ligand-analog represented by R include, for example, procainamide, thyroxine, quinidine and the aminoglycoside antibiotics. Illustrative of ligands whose amino derivatives are useful as ligand-analog include theophylline, valproic acid, phenobarbital, phenytoin, primidone, disopyramide, digoxin, chloramphenicol, salicylate, acetaminophen, carbamazepine, desimpramine and nortriptyline. In addition, a ligand may be structurally modified by the addition or deletion of one or more functional groups to form a ligand-analog, while retaining the necessary epitope sites for binding to an antibody. However, it is preferred that such modified ligand-analogs be bonded to a carboamidosulfonylaminofluorescein moiety through an imino or oxy group.

The tracers of the present invention are prepared in accordance with known techniques. When X is a sulfonyl group,

the tracers of the present invention are prepared by reacting a compound of the formula:

R—Y  (II)

wherein R is above-defined and Y is an aromatic hydrogen, preferably bonded to a phenyl ring, with chlorosulfonic acid to produce a chlorosulfonyl ligand-analog of the formula:

  (III)

The chlorosulfonyl ligand-analog is reacted with an aminofluorescein of the formula:

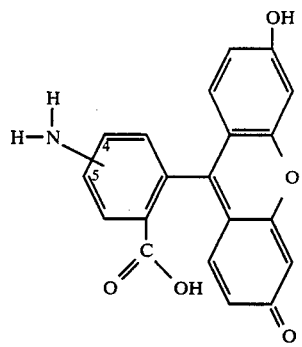  (IV)

wherein the amino group is bonded to the 4 or 5 position of the benzoic acid ring; in the presence of an inert solvent to yield a tracer of the present invention of the formula:

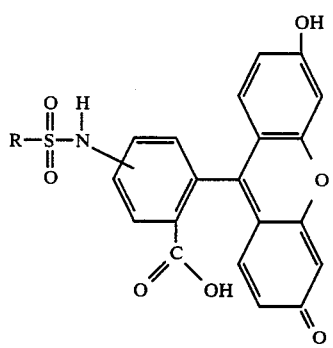  (V)

When X is an oxalyl group,

the tracers of the present invention are prepared by reacting a compound of the formula

R—Z  (VI)

wherein R is above-defined and Z is a hydrogen bonded to a reactive nitrogen (primary or secondary amine), with methyloxalylchloride to yield a methoxyoxalyl ligand-analog which is hydrolyzed in the presence of a base to yield hydroxyoxalyl ligand-analog of the formula

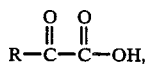  (VII)

The hydroxyoxalyl ligand-analog is reacted with an aminofluorescein of formula (IV) in the presence of a coupling agent, such as, 1-ethyl-3-(3'-dimethylaminopropyl)-carbodiimide hydrochloride, and an inert solvent to yield a tracer of the present invention of the formula:

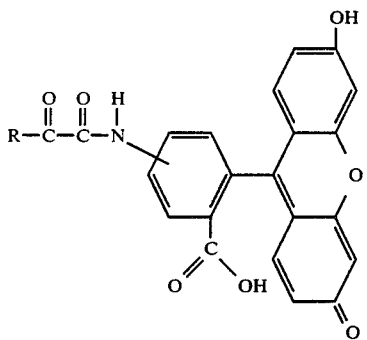

(VIII)

When X is a carboamidosulfonyl,

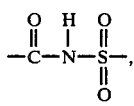

the tracers of the present invention are prepared by reacting a compound of the formula

 R—W                                    (IX)

wherein R is above-defined and W is a hydrogen bonded to a reactive nitrogen (primary or secondary amine) or to a hydroxy oxygen; with chlorosulfonylisocyanate to yield a chlorosulfonamidocarbonyl-ligand-analog derivative of the formula

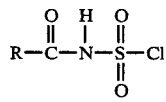                                    (X)

The chlorosulfonamidocarbonyl-ligand-analog derivative is reacted with an aminofluorescein of formula (IV) to yield the tracers of the present invention of the formula:

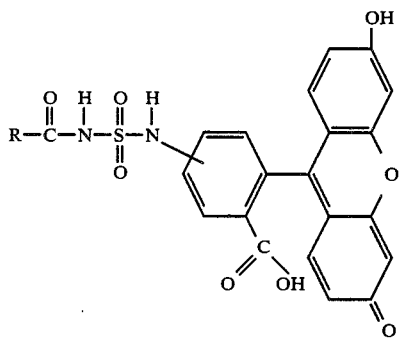

The temperature at which the reaction for preparing the tracers of this invention proceeds is not critical. The temperature should be one which is sufficient so as to initiate and maintain the reaction. Generally, for convenience and economy, room temperature is sufficient. In preparing the tracers of the present invention, the ratio of reactants is not narrowly critical. For example, for each mole of a compound of formula (II), one should employ two moles of chlorosulfonic acid to obtain a reasonable yield. It is preferred to employ an excess of chlorosulfonic acid for ease of reaction and recovery of the reaction products.

The compounds of formula (IV) employed as starting materials in the production of the tracers of this invention are either commercially available or prepared in accordance with known techniques.

For ease of handling and recovery of product, the process for preparing the tracers of the present invention is conducted in the presence of an inert solvent. Suitable inert solvents include those solvents which do not react substantially with the starting materials and are sufficient to dissolve the starting materials and include for example, acetone, chloroform, pyridine, and the like. In order to provide maximum product yields, the reaction preferably proceeds under neutral or basic conditions. Suitable bases include for example triethylamine, pyridine, and the like. The reaction products are generally purified using either thin-layer or column chromatography prior to application in the methods of the present invention.

In accordance with the method of the present invention, a sample containing the ligand to be determined is intermixed with a biologically acceptable salt of a tracer of formula (I) and an antibody specific for the ligand and tracer. The ligand present in the sample and the tracer compete for limiting antibody sites resulting in the formation of ligand-antibody and tracer-antibody complexes. By maintaining constant the concentration of tracer and antibody, the ratio of ligand-antibody complex to tracer-antibody complex that is formed is directly proportional to the amount of ligand present in the sample. Therefore, upon exciting the mixture with fluorescent light and measuring the polarization of the fluorescence emitted by a tracer and a tracer-antibody complex, one is able to quantitatively determine the amount of ligand in the sample.

In theory, the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of a ligand, the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertical component of the emitted light, the polarization of fluorescence of the reaction mixture may be accurately determined. The precise relationship between polarization and concentration of the ligand to be determined is established by measuring the polarization values of calibrators with known concentrations. The concentration of the ligand can be extrapolated from a standard curve prepared in this manner.

The pH at which the method of the present invention is practiced must be sufficient to allow the tracers of formula (I) to exist in their ionized state. The pH may range from about 3 to 12, more usually in the range of from 5 to 10, most preferably from about 6 to 9. Various buffers may be used to achieve and maintain the pH during the assay procedure. Representative buffers include borate, phosphate, carbonate, tris, barbital, and the like. The particular buffer employed is not critical to the present invention, but in an individual assay, a specific buffer may be preferred in view of the antibody employed and ligand to be determined. The cation portion of the buffer will generally determine the cation portion of the tracer salt in solution.

The methods of the present invention are practiced at moderate temperatures and preferably at a constant temperature. The temperature will normally range from about 0° to 50° C., more usually from about 15° to 40° C.

The concentration of ligand which may be assayed will generally vary from about $10^{-2}$ to $10^{-13}$M, more usually from about $10^{-4}$ to $10^{-10}$M. Higher concentrations of ligand may be assayed upon dilution of the original sample.

In addition to the concentration range of ligand of interest, considerations such as whether the assay is qualitative, semiquantitative, or quantitative, the equipment employed, and the characteristics of the tracer and antibody will normally determine the concentration of the tracer and antibody to be employed. While the concentration of ligand in the sample will determine the range of concentration of the other reagents, i.e., tracer and antibody, normally to optimize the sensitivity of the assay, individual reagent concentrations will be determined empirically. Concentrations of the tracer and antibody are readily ascertained by one of ordinary skill in the art.

As previously mentioned the preferred tracers of the present invention are prepared from 5-aminofluorescein or 4-aminofluorescein and exist preferably as isomers of the formula:

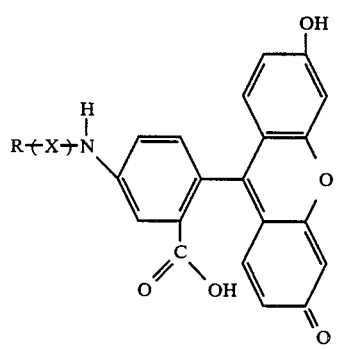

(XII)

or

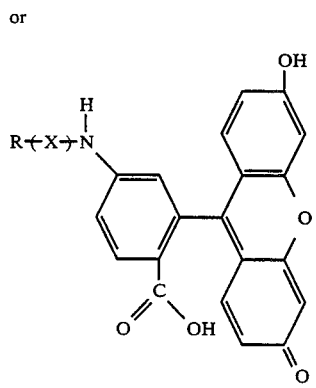

(XIII)

wherein R and X are above defined.

The following illustrative, nonlimiting examples will serve to further demonstrate to those skilled in the art the manner in which specific tracers within the scope of this invention may be prepared. The symbol [AF] appearing in the structural formulas illustrating the compounds prepared in the following examples, represents a moiety of the formula:

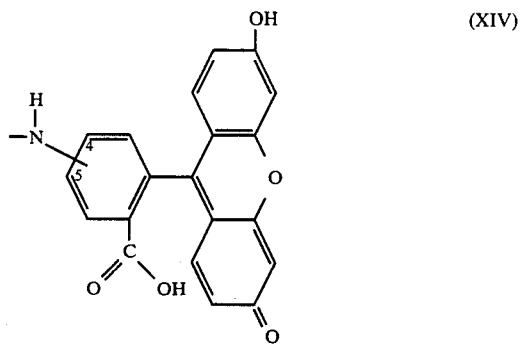

(XIV)

wherein the imino nitrogen is attached to the 4 or 5 position in the above formula depending on the specific aminofluorescein isomer employed as the starting material.

EXAMPLE I

To 0.71 g of lidocaine was added 2.8 g of chlorosulfonic acid and the resultant mixture was heated at 60° C. for one hour. The reaction mixture was cooled and crushed ice and water were added to the mixture to dissipate any unreacted chlorosulfonic acid. The resultant aqueous solution was neutralized to pH 7 using sodium hydroxide. The resultant product was extracted twice with 10 ml portions of methylene chloride. The methylene chloride extracts were combined, dried over sodium sulfate, filtered and evaporated to dryness to yield 100 mg of a mixture of meta- and para-chlorosulfonyl lidocaine as a gummy oil. To a solution containing 5 mg of 4-aminofluorescein in 0.5 ml of pyridine was added 5 mg of the above chlorosulfonyllidocaine mixture. After ten minutes, a crude product formed. The crude product was purified by thin-layer chromatography using silica gel and chloroform, then a mixture of chloroform: acetone (1:1) and finally a mixture of chloroform:methanol (1:1) developing solvents to yield a mixture of sulfonyllidocaine-aminofluorescein conjugate of the general formula:

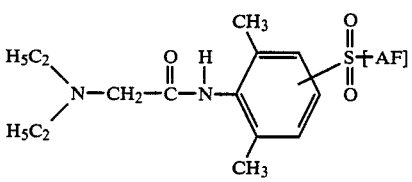

EXAMPLE II

To 1.2 g of phenobarbital was slowly added 4.5 g of chlorosulfonic acid and the resultant mixture was heated at 60° C. for one hour. The reaction mixture was cooled and crushed ice and water were added to the mixture to dissipate any unreacted chlorosulfonic acid. The reaction mixture was then filtered to yield a white precipitate which was rinsed with water and dried in a vacuum desiccator to yield 0.8 g of a mixture of meta- and para-chlorosulfonylphenobarbital having a melting point of 190°-195° C. To a solution containing 5 mg of 5-aminofluorescein in 0.5 ml of pyridine was added 5 mg of the above mixture of chlorosulfonylphenobarbital. After 10 minutes, a crude product had formed and was purified twice employing thin-layer chromatography techniques employing silica gel and a mixture of chloroform:methanol (2:1) as a developing solvent to yield a sulfonylphenobarbital-aminofluorescein conjugate of the formula:

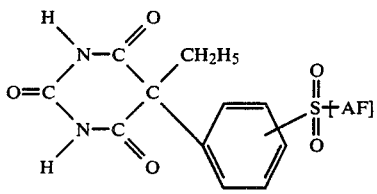

EXAMPLE III

To 2 g of α-phenethyl-α-methylsuccinimide was dropwise added 2.5 g of chlorosulfonic acid and the resultant mixture was stirred at 26° C. for one hour. Crushed ice and water were added to the mixture to dissipate any unreacted chlorosulfonic acid. A reaction product which had formed was extracted twice with 10 ml portions of chloroform. The chloroform extracts were combined, dried over sodium sulfate and evaporated to yield a heavy oil. The oil was crystallized from a mixture of toluene and petroleum ether to yield 0.29 g of a mixture of α-(meta- and para-chlorosulfonylphenethyl)-α-methylsuccinimide having a melting point of 145°–150° C. To a solution containing 5 mg of 4-aminofluorescein in 0.5 ml of pyridine was added 5 mg of the above mixture to α-(chlorosulfonylphenethyl)-α-methylsuccinimide. After 10 minutes, a crude product had formed which was purified twice employing thin-layer chromatographic techniques utilizing silica gel and a mixture of chloroform:methanol (2:1) as a developing solvent to yield a mixture of α-(sulfonylphenethyl)-α-methylsuccinimide-aminofluorescein conjugate of the formula:

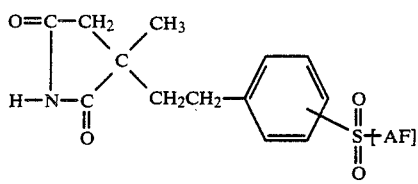

EXAMPLE IV

To a solution containing 2 g of iminostilbene and 2 ml of triethylamine in 50 ml of chloroform was added 1.5 g of methyloxalylchloride. The resultant mixture was refluxed for one hour and then evaporated to dryness. The residue was taken up in 50 ml of chloroform and then extracted with 50 ml of water. The chloroform layer was evaporated to dryness. To the residue was added 100 ml of 2N sodium hydroxide and the resultant mixture was refluxed for 30 minutes. The mixture was cooled to room temperature and then extracted with 50 ml of chloroform. The aqueous layer was acidified to pH 1 using concentrated hydrochloric acid and then extracted with 100 ml of ether. The organic extract was dried over sodium sulfate and evaporated to dryness. The residue was taken up in 50 ml of methanol and triturated with water to yield a crop of crystals. The mixture was filtered and the crystals were cooled for 16 hours to yield 2.4 g of a N-hydroxyoxalyl-iminostilbene (melting point 162°–163° C.).

To 5 mg of the N-hydroxyoxalyl-iminostilbene was added a solution containing 5 mg of 4-aminofluorescein in 0.5 ml of pyridine. The reaction was allowed to proceed for two hours at 26° C. to yield a crude product. The crude product was purified using thin-layer chromatography employing silica gel and a developing solution consisting of a mixture of chloroform:acetone (1:1) to yield an N-oxalyl-iminostilbene-aminofluorescein conjugate of the formula:

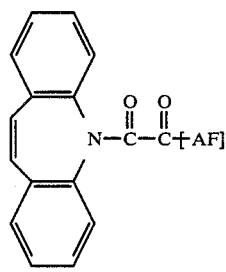

The following tracers were also prepared in accordance with the above procedures:

EXAMPLE V

Sulfonylprimidone-aminofluorescein conjugates

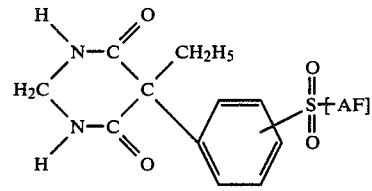

EXAMPLE VI

Para-methyl-meta-sulfonylprimidone-aminofluorescein conjugate

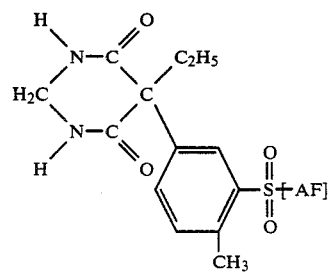

EXAMPLE VII

Para-methyl-meta-sulfonylphenobarbital-aminofluorescein conjugate

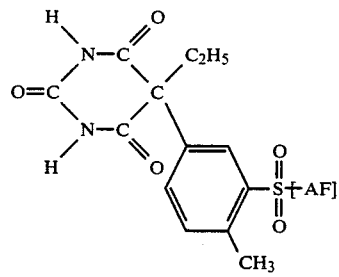

EXAMPLE VIII

5-Sulfonylphenyl-5-ethylhydantoin-aminofluorescein conjugate

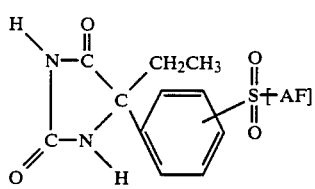

EXAMPLE IX

α-(Sulfonylphenyl)-α-methylsuccinimide-aminofluorescein conjugate

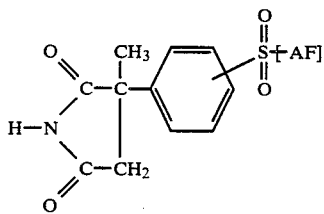

EXAMPLE X

O-sulfonamidocarbonylpropranolol-aminofluorescein conjugate

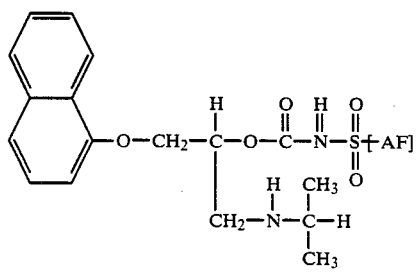

EXAMPLE XI

N-sulfonamidocarbonyl-iminostilbene-aminofluorescein conjugate

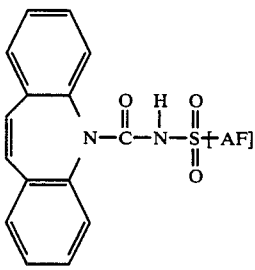

EXAMPLE XII

N-sulfonamidocarbonyl-procainamide-aminofluorescein conjugate

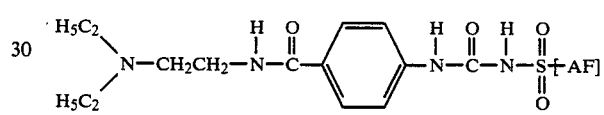

EXAMPLE XIII

O-sulfonamidocarbonyl-chloramphenicol-aminofluorescein conjugate

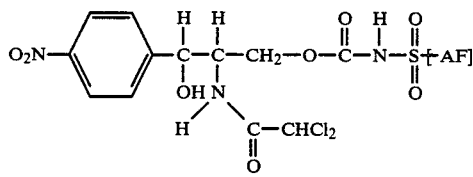

EXAMPLE XIV

N-sulfonamidocarbonyl-disopyramide-aminofluorescein conjugate

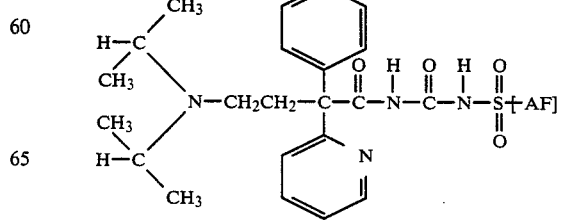

EXAMPLE XV

O-sulfonamidocarbonyl-quinidine-aminofluorescein conjugate

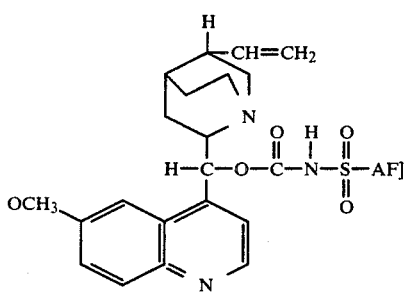

EXAMPLE XVI

O-oxalyl-propranolol-aminofluorescein conjugate

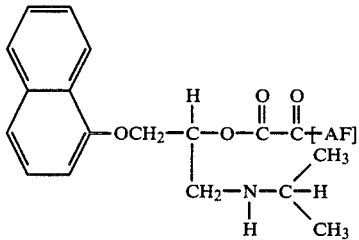

EXAMPLE XVII

N-oxalyl-procainamide-aminofluorescein conjugate

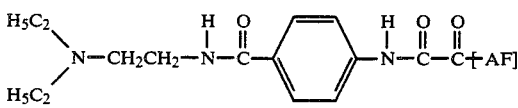

EXAMPLE XVIII

N-acetyl-N'-desethyl-N'-oxalyl-procainamide-aminofluorescein conjugate

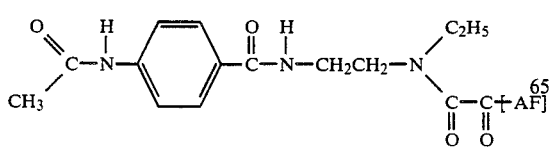

EXAMPLE XIX

N-oxalyl-nortriptyline-aminofluorescein conjugate

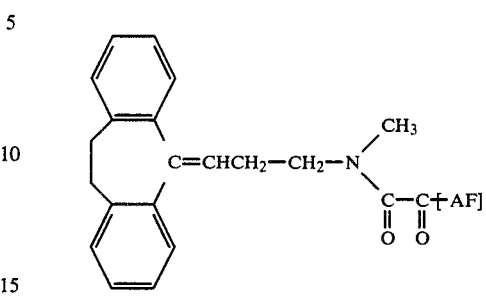

EXAMPLE XX

N-oxalyl-iminodibenzyl-aminofluorescein conjugate

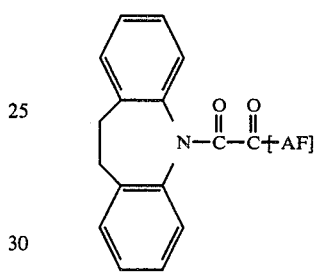

As previously mentioned, the tracers of the present invention are effective reagents for use in fluorescence polarization immunoassays. The following Examples illustrate the suitability of tracers of the present invention in immunoassays employing fluorescence polarization techniques. Such assays are conducted in accordance with the following general procedure:

(1) A measured volume of standard or test serum is delivered into a test tube and diluted with buffer;

(2) A known concentration of a tracer of the present invention optionally containing a surfactant is then added to each tube;

(3) A known concentration of antisera is added to the tubes;

(4) The reaction mixture is incubated at room temperature; and (5) The amount of tracer bound to antibody is measured by fluorescence polarization techniques as a measure of the amount of ligand in the sample.

EXAMPLE XXI

Lidocaine Assay

Materials (1) Buffer: 0.1M phosphate, pH 7.5, containing 0.01% (weight/volume) sodium azide and 0.01% (weight/volume) bovine gamma globulin (hereinafter referred to as "BGG buffer").

(2) Tracer: Sulfonyllidocaine-aminofluorescein conjugate (prepared in Example I) at a concentration of $2.34 \times 10^{-7}$M in 0.1M tris hydrochloride buffer, pH 7.8, containing 0.1% (weight/volume) sodium dodecyl sulfate, 0.01% (weight/volume) bovine gamma globulin and 0.01% (weight/volume) sodium azide.

(3) Antibody: Rabbit antiserum to lidocaine diluted 1 to 80 in BGG buffer.

(4) Standards or unknowns: Human serum (or other biological fluid) containing lidocaine in a concentration range of 0 to 10 μg/ml.
(5) Fluorescence polarimeter: Instrument capable of measuring the polarization of fluorescence of a $1 \times 10^{-9}$M fluorescein solution to ±0.001 polariaztion units.

Protocol (1) To 20 μl of standards and unknowns add 200 μl of BGG buffer.
(2) To 20 μl of each diluted standard and unknown in a culture tube, add 200 μl of BGG buffer.
(3) To each culture tube containing diluted standard and unknown add 40 μl of tracer and 1000 μl of BGG buffer.
(4) Then add 40 μl of antibody and 1000 μl of BGG buffer to each culture tube.
(5) Mix the reagents and incubate the culture tubes containing standards and unknowns for approximately 15 minutes at 23° C.
(6) Measure the fluorescence polarization of all tubes. Typical results for standard samples are presented in Table I.

TABLE I

| Lidocaine Concentration (μg/ml) | Polarization |
| --- | --- |
| 0 | 0.224 |
| 0.5 | 0.186 |
| 1.0 | 0.162 |
| 2.5 | 0.124 |
| 5.0 | 0.094 |
| 10.0 | 0.071 |

The polarization values decreases as the concentration of lidocaine is increased, allowing construction of a standard curve. Unknowns treated in an identical manner may be quantitated by reference to the standard curve.

EXAMPLE XXII

Phenobarbital Assay

Materials (1) BGG buffer
(2) Tracer: (para-methyl-meta-sulfonyl)phenobarbital-aminofluorescein conjugate (prepared in Example VII) at a concentration of $5.75 \times 10^{-8}$M in 5.75% sodium cholate.
(3) Antibody: Rabbit antiserum to phenobarbital diluted 1 to 78.3 in BGG buffer.
(4) Standards or unknowns: Human serum (or other biological fluid) containing phenobarbital in a concentration range of 0 to 80 μg/ml.
(5) Fluorescence polarimeter: Instrument capable of measuring the polarization of fluorescence of a $1 \times 10^{-9}$M fluorescein solution to ±0.001 polarization units.

Protocol (1) To 20 μl of standards and unknowns add 200 μl of BGG buffer.
(2) To 20 μl of each diluted standard and unknown in a culture tube, add 200 μl of BGG buffer.
(3) To each culture tube containing diluted standard and unknown add 40 μl of tracer and 1000 μl of BGG buffer.
(4) Then add 40 μl of antibody and 1000 μl of BGG buffer to each culture tube.
(5) Mix the reagents and incubate the culture tubes containing standards and unknowns for approximately 15 minutes at 23° C.
(6) Measure the fluorescence polarization of all tubes. Typical results for standard samples are presented in Table II.

TABLE II

| Phenobarbital Concentration (μg/ml) | Polarization |
| --- | --- |
| 0 | 0.155 |
| 10 | 0.108 |
| 20 | 0.092 |
| 40 | 0.074 |
| 80 | 0.060 |

The polarization values decrease as the concentration of phenobarbital is increased, allowing construction of a standard curve. Unknowns treated in an identical manner may be quantitated by reference to the standard curve.

EXAMPLE XXIII

Carbamazepine Assay

Materials (1) BGG buffer.
(2) Tracer: N-oxalyliminostilbene-aminofluorescein conjugate (prepared in Example IV) at a concentration of 2 nM in BGG buffer containing 0.2% (weight/volume) sodium cholate.
(3) Antibody: Rabbit antiserum to carbamazepine diluted 1 to 3040 in BGG buffer.
(4) Standards or unknowns: Human serum (or other biological fluid) containing carbamazepine in a concentration range of 0 to 20 μg/ml.
(5) Fluorescence polarimeter: Instrument capable of measuring the polarization of fluorescence of $1 \times 10^{-9}$M fluorescein solution to ±0.001 polarization units.

Protocol (1) To 10 μl of standards and unknowns add 300 μl of BGG buffer.
(2) To 10 μl of each diluted standard and unknown in a culture tube, add 300 μl of BGG buffer.
(3) Add 1 ml of tracer to each culture tube.
(4) Then add 1.0 ml of antibody to each culture tube.
(5) Mix the reagents and incubate the culture tubes containing standards and unknowns for approximately 15 minutes at 23° C.
(6) Measure the fluorescence polarization of all tubes. Typical results for standard samples are presented in Table III.

TABLE III

| Carbamazepine Concentration μg/ml | Polarization |
| --- | --- |
| 0 | 0.224 |
| 2 | 0.108 |
| 4 | 0.135 |
| 8 | 0.105 |
| 12 | 0.088 |
| 20 | 0.077 |

The polarization values decrease as the concentration of carbamazepine is increased, allowing construction of a standard curve. Unknowns treated in an identical manner may be quantitated by reference to the standard curve.

The following table summarizes the various fluorescence polarization immunoassays that have been carried out in accordance with the above-described procedures employing tracers prepared in the preceding Examples. The tracers employed are identified by Example number and the specific ligand(s) determined are indicated.

| Tracer Prepared In Example Number | Ligand(s) Assayed |
|---|---|
| I | Lidocaine |
| II | Phenobarbital |
| III | Ethosuximide |
| IV | Carbamazepine |
| V | Primidone |
| VI | Primidone |
| VII | Phenobarbital |
| VIII | Phenytoin |
| IX | Ethosuximide |
| X | Propanolol |
| XI | Carbamazepine |
| XII | Procainamide |
| XIII | Chloramphenicol |
| XIV | Disopyramide |
| XV | Quinidine |
| XVI | Propanolol |
| XVII | Procainamide |
| XVIII | N—Acetyl Procainamide |
| XIX | Desipramine; Imipramine |
| XX | Nortriptyline;Amitriptyline |

As evident from the above results, the tracers of the present invention are effective reagents in fluorescence polarization immunoassays. In addition to the properties mentioned above, the tracers of the present invention possess a high degree of thermal stability, a high degree of bound polarization, high quantum yields and are relatively easy to produce and purify.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A compound of the formula

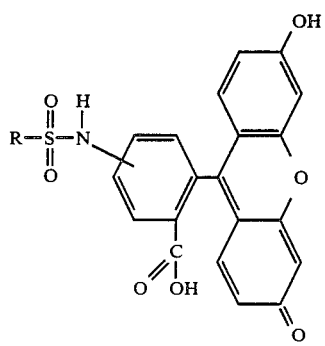

wherein

R is a ligand-analog of an aromatic carbon-containing ligand having a molecular weight in a range of 100 to 2000 wherein said ligand-analog has at least one common epitope with said ligand so as to be specifically recognizable by a common antibody and said ligand-analog has an aromatic carbon by which the ligand-analog is attached to the sulfonamidofluorescein moiety;

and biologically acceptable salts thereof.

2. A compound according to claim 1 of the formula:

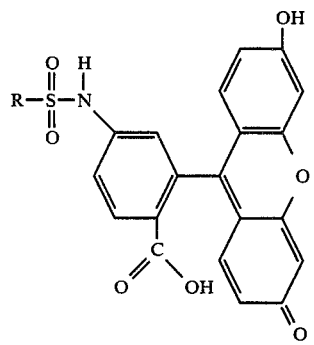

or

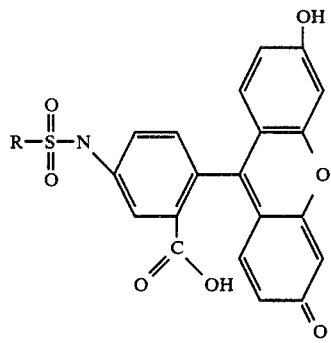

and biologically acceptable salts thereof.

3. A compound according to claim 2 wherein R is derived from a ligand selected from the group consisting of steroids, hormones, antiasthmatics, antineoplastics, antiarrhythmics, anticonvulsants, antibiotics; antiarthritics, antidepressants and cardiac glycosides.

4. A compound according to claim 3 wherein R is derived from an antiarrhythmic.

5. A compound according to claim 4 wherein R is derived from lidocaine.

6. The compound of claim 1 having the structural formula

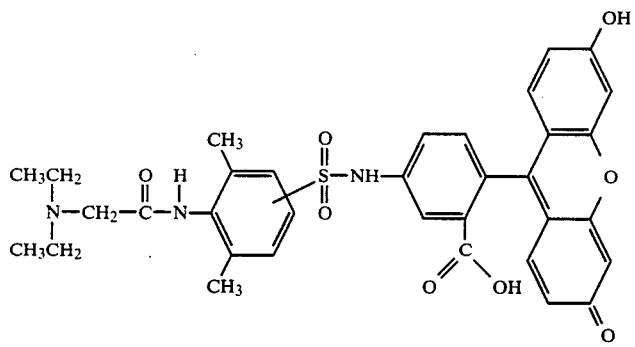

7. A compound according to claim 3 wherein R is derived from an anticonvulsant.

8. A compound according to claim 7 wherein R is derived from phenytoin.

9. A compound according to claim 8 wherein R is

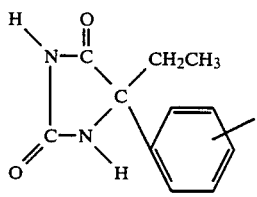

10. A compound according to claim 7 wherein R is derived from primidone.

11. A compound according to claim 7 wherein R is

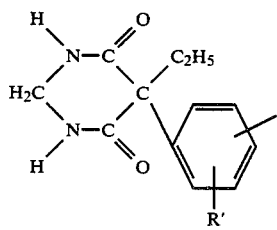

wherein R' is alkyl having from one to four carbon atoms.

12. A compound according to claim 7 wherein R is derived from ethosuccimide.

13. A compound according to claim 12 wherein R is

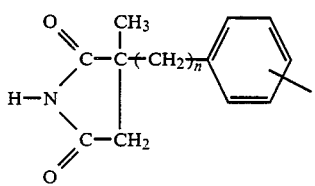

wherein n is an integer of from 0 to 3.

14. A compound of the formula

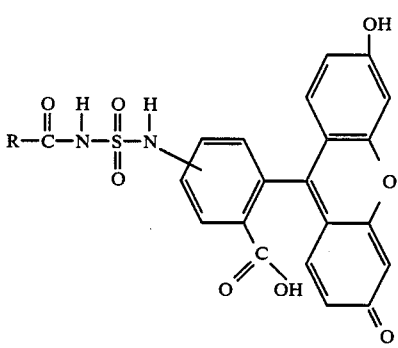

wherein
R is a ligand-analog having a molecular weight in range of 100 to 2000 wherein said ligand-analog has at least one common epitope with said ligand so as to be specifically recognizable by a common antibody and said ligand-analog is attached to the carboamidosulfonylaminofluorescein moiety through a hydroxy oxygen or a reactive amine;
and biologically acceptable salts thereof.

15. A compound according to claim 14 of the formula

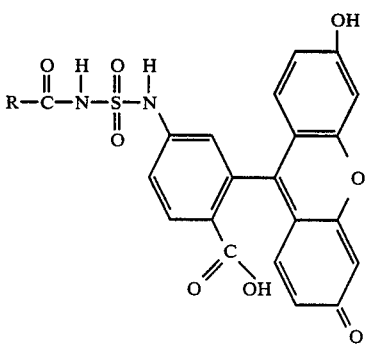

or

-continued

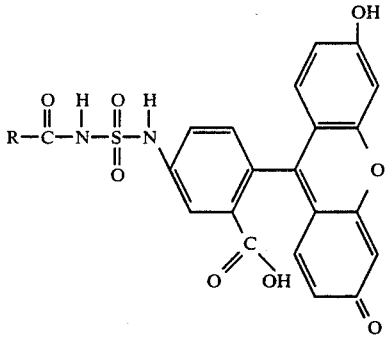

and biologically acceptable salts thereof.

16. A compound according to claim 15 wherein R is derived from a ligand selected from the group consisting of steroids, hormones, antiasthmatics, antineoplastics, antiarrhythmics, anticonvulsants, antibiotics, antiarthritics, antidepressants and cardiac glycosides.

17. A compound according to claim 16 wherein R is derived from an anticonvulsant.

18. A compound according to claim 17 wherein R is derived from carbamazepine.

19. A compound of the formula wherein R is

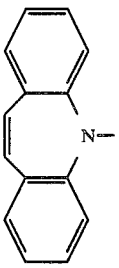

20. A compound according to claim 16 wherein R is derived from an antiarrhythmic.

21. A compound according to claim 20 wherein R is derived from procainamide.

22. A compound according to claim 20 wherein R is derived from propranolol.

23. A compound of the formula

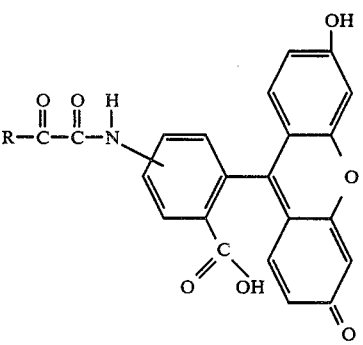

wherein

R is a ligand-analog having a molecular weight in a range of 100 to 2000 wherein said ligand-analog has at least one common epitope with said ligand so as to be specifically recognizable by a common antibody and said ligand-analog has a reactive nitrogen by which the ligand-analog is attached to the oxalylaminofluorescein moiety;

and biologically acceptable salts thereof.

24. A compound of the formula:

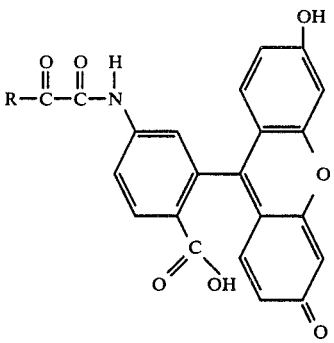

or

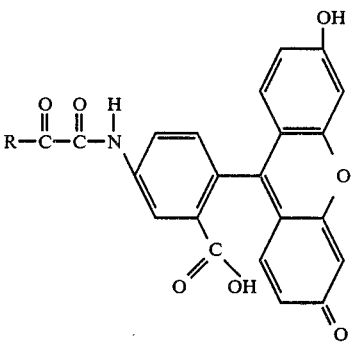

and biologically acceptable salts thereof.

25. A compound according to claim 24 wherein R is derived from a ligand selected from the group consisting of steroids, hormones, antiasthmatics, antineoplastics, antiarrhythmics, anticonvulsants, antibiotics, antiarthritics, antidepressants and cardiac glycosides.

26. A compound according to claim 25 wherein R is derived from an antidepressant.

27. A compound according to claim 26 wherein R is derived from a tricyclic drug.

28. A compound according to claim 27 wherein R is derived from nortriptyline, amitriptyline, imipramine or desipramine.

29. A compound according to claim 28 wherein R is derived from an anticonvulsant.

30. A compound according to claim 29 wherein R is derived from carbamazepine.

31. A compound according to claim 30 wherein R is

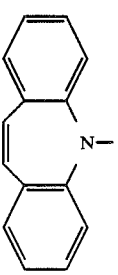

32. A method for determining ligands in a sample comprising intermixing with said sample a biologically acceptable salt of a tracer of the formula:

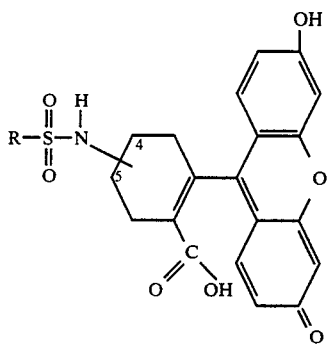

wherein

R is a ligand-analog having a molecular weight in a range of 100 to 2000 wherein said ligand-analog has at least one common epitope with said ligand so as to be specifically recognizable by a common antibody and said ligand-analog has an aromatic carbon by which the ligand-analog is attached to the sulfonamidofluorescein moiety;

and an antibody capable of specifically recognizing said ligand and said tracer and then determining the amount of tracer bound to antibody by fluorescence polarization techniques as a measure of the amount of ligand in the sample.

33. A method according to claim 32 wherein the sulfonamido group bonded to the R group is also bonded to the 4- or 5-position of the fluorescein moiety.

34. A method according to claim 33 wherein said ligand is a steroid, hormone, antiasthmatic, antineoplastic, antiarrhythmic, anticonvulsant, antibiotic, antiarthritic, antidepressant, cardiac glycoside or a metabolite thereof.

35. A method according to claim 34 wherein R has a molecular weight in a range of 50 to 4000.

36. A method according to claim 35 wherein R has a molecular weight in a range of 100 to 2000.

37. A method according to claim 36 wherein said ligand is an antiarrhythmic.

38. A method according to claim 37 wherein said antiarrhythmic is lidocaine.

39. A method according to claim 38 wherein said ligand is an anticonvulsant.

40. A method according to claim 39 wherein said anticonvulsant is phenytoin.

41. A method according to claim 39 wherein said anticonvulsant is primidone.

42. A method according to claim 39 wherein said anticonvulsant is ethosuximide.

43. A method for determining ligands in a sample comprising intermixing with said sample a biologically acceptable salt of a tracer of the formula:

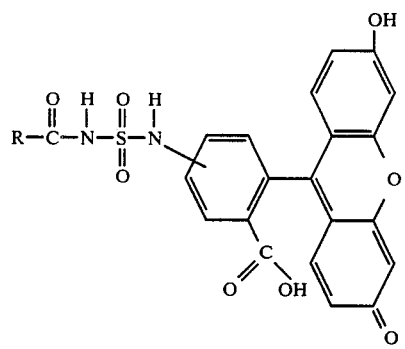

wherein

R is a ligand-analog having a molecular weight in a range of 100 to 2000 wherein said ligand-analog has at least one common epitope with said ligand so as to be specifically recognizable by a common antibody and said ligand-analog is attached to the carboamidosulfonylamino group moiety through a hydroxy oxygen or a reactive amine;

and biologically acceptable salts thereof.

44. A method according to claim 43 wherein the carboamidosulfonylamino group bonded to the R group is also bonded to the 4- or 5-position of the fluorescein moiety.

45. A method according to claim 44 wherein said ligand is a steroid, hormone, antiasthmatic, antineoplastic, antiarrhythmic, anticonvulsant, antibiotic, antiarthritic, antidepressant, cardiac glycoside or a metabolite thereof.

46. A method according to claim 45 wherein R has a molecular weight in a range of 50 to 4000.

47. A method according to claim 46 wherein R has a molecular weight in a range of 100 to 2000.

48. A method according to claim 47 wherein said ligand is an anticonvulsant.

49. A method according to claim 48 wherein said anticonvulsant is carbamazepine.

50. A method for determining ligands in a sample comprising intermixing with said sample a biologically acceptable salt of a tracer of the formula:

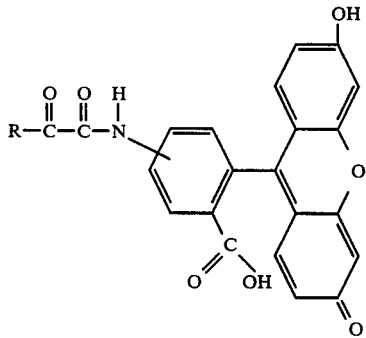

wherein

R is a ligand-analog having a molecular weight in a range of 100 to 2000 wherein said ligand-analog has at least one common epitope with said ligand so as to be specifically recognizable by a common antibody and said ligand-analog has a reactive nitrogen by which the ligand-analog is attached to the oxalylaminofluorescein moiety;

and biologically acceptable salts thereof.

51. A method according to claim 50 wherein the oxalylamino group bonded to the R group is also bonded to the 4- or 5-position of the fluorescein moiety.

52. A method according to claim 51 wherein said ligand is a steroid, hormone, antiashtmatic, antineoplastic, antiarrhythmic, anticonvulsant, antibiotic, antiarthritic, antidepressant, cardiac glycoside or a metabolite thereof.

53. A method according to claim 52 wherein R has a molecular weight in a range of 50 to 4000.

54. A method according to claim 53 wherein R has a molecular weight in a range of 100 to 2000.

55. A method according to claim 54 wherein said ligand is an anticonvulsant.

56. A method according to claim 55 wherein said anticonvulsant is carbamazepine.

* * * * *

UNITED STATES PATENT AND TRADEMARK OFFICE
CERTIFICATE OF CORRECTION

PATENT NO. : 4,585,862
DATED : April 29, 1986
INVENTOR(S) : C. Wang, S. Stroupe, M. Jolley It is certified that error appears in the above—identified patent and that said Letters Patent is hereby corrected as shown below:

Please cancel Claims 7-56, inclusive.

Signed and Sealed this

Third Day of March, 1987

*Attest:*

DONALD J. QUIGG

*Attesting Officer*       *Commissioner of Patents and Trademarks*